(12) United States Patent
Bates et al.

(10) Patent No.: US 8,332,186 B2
(45) Date of Patent: Dec. 11, 2012

(54) METHOD AND APPARATUS FOR GENERATING A MODEL OF AN OBJECT

(75) Inventors: Susan Bates, Bebington (GB); Robert Lindsay Treloar, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 354 days.

(21) Appl. No.: 12/593,023

(22) PCT Filed: Mar. 11, 2008

(86) PCT No.: PCT/EP2008/052860
§ 371 (c)(1),
(2), (4) Date: Feb. 1, 2010

(87) PCT Pub. No.: WO2008/116743
PCT Pub. Date: Oct. 2, 2008

(65) Prior Publication Data
US 2011/0131014 A1    Jun. 2, 2011

(30) Foreign Application Priority Data

Mar. 28, 2007  (GB) .................................. 0706048.6

(51) Int. Cl.
*G06F 17/50* (2006.01)
(52) U.S. Cl. ........................................................ 703/1
(58) Field of Classification Search .................. 703/1, 6; 700/98; 433/24, 63, 68, 69, 213, 223; 382/120
See application file for complete search history.

(56) References Cited

U.S. PATENT DOCUMENTS

| | | | |
|---|---|---|---|
| 5,006,065 A * | 4/1991 | Waysenson | 433/63 |
| 5,605,459 A | 2/1997 | Kuroda et al. | |
| 6,068,482 A * | 5/2000 | Snow | 433/223 |
| 6,621,491 B1 | 9/2003 | Baumrind et al. | |
| 6,726,478 B1 * | 4/2004 | Isiderio et al. | 433/69 |
| 2001/0038705 A1 | 11/2001 | Rubbert et al. | |
| 2002/0055800 A1 * | 5/2002 | Nikolskiy et al. | 700/98 |

(Continued)

FOREIGN PATENT DOCUMENTS

| WO | 02/083257 A2 | 10/2002 |
|---|---|---|
| WO | 2005/004743 A1 | 1/2005 |

OTHER PUBLICATIONS

International Search Report PCT/EP208/052860.

(Continued)

*Primary Examiner* — Kandasamy Thangavelu
(74) *Attorney, Agent, or Firm* — Ellen Plotkin

(57) ABSTRACT

A method of generating a model of a real object derived from a model of a second object, the model of the second object being defined by an array of data points, a number of identifiable components and a number of further components, comprises measuring parameters of corresponding identifiable components of a real object corresponding to the identifiable components in the model the second object. An array of data points defining a first model of the real object is generated the measured parameters. A further model of the real object is generated by substantially aligning the model of the second object with the first model of the real object, placing identifiable components represented in the model of the second object into positions corresponding to positions of equivalent components in the real object as defined by the measured parameters, placing the further components represented in the model of the second object into positions on the first model of the real object to represent corresponding components in the real object and adjusting the positions of one or more of the components placed on the first model of the real object to generate the further model of the real object. There is also disclosed an apparatus for generating a model of a real object.

23 Claims, 5 Drawing Sheets

U.S. PATENT DOCUMENTS

| | | | |
|---|---|---|---|
| 2002/0064759 A1* | 5/2002 | Durbin et al. | 433/213 |
| 2003/0169913 A1 | 9/2003 | Kopelman et al. | |
| 2005/0203726 A1* | 9/2005 | Marshall | 703/11 |
| 2007/0072145 A1* | 3/2007 | Kopelman et al. | 433/24 |
| 2007/0190481 A1* | 8/2007 | Schmitt | 433/68 |
| 2007/0292004 A1* | 12/2007 | Peters | 382/120 |

OTHER PUBLICATIONS

GB Search Report—GB0706048.6.

"Dentition planning with image-based occlusion analysis"—by Ferenc Pongracz et al., Internatinal Journal of Computer Assisted Radiology and Surgery: A Jou4rnal for Interdisciplinary Research, Development and Applications of Image Guided Diagnosis and Therapy, Springer-Verlag, BE, vol. 1, No. 3, Oct. 28, 2006, pp. 1439-156; XP019456767.

"A Morphable Model for the Synthesis of 3D Faces"—Blanz et al., Computer Graphics, Siggraph 99 Conference Proceedings, Los Angeles, CA, Aug. 8, 1999, pp. 187-194, XP001032901.

"Robust Euclidean alignment of 3D point sets: the trimmed iterative closest point algorithm"—Chetverikov et al., Image and Vision Computing, Guildford, GB, vol. 23, No. 3, Mar. 1, 20055, pp. 299-309, XP004737048.

* cited by examiner

METHOD AND APPARATUS FOR GENERATING A MODEL OF AN OBJECT

The present invention is directed to a method of generating a model of a real object and an apparatus for generating a model of an object, the object preferably being a jaw with a set of teeth located therein.

It is well known that numerous dental problems experienced by individuals may be due to incorrect toothbrush usage arising from poor brushing techniques and/or the design of the toothbrush being used, both of which may result in the brush failing to contact certain areas of the individual's teeth. The applicant's published International patent application WO 02/083257 is directed to a computer based system for capturing and displaying the tooth brushing behaviour of an individual. In this system, a set of two realistic computer models are generated for each individual, one each for the upper and lower jaw. In this instance, the term 'computer model' means a geometry defined as a set of connected polygons, stored within the computer, which can be rendered into a visual representation on the computer screen. These models are needed for two reasons, firstly in order to make measurements relating to tooth brushing effectiveness, and secondly to create believable on-screen feedback for the individual.

In WO 02/083257 one approach to generating these computer models is described as using teeth-casts. The tooth geometries were described predominantly as being created by making physical teeth-casts using traditional dental techniques and then scanning them to a high level of detail geometry using laser scanning techniques.

In some instances, such conventional methods of creating and scanning teeth-casts are impractical in light of time and cost constraints. In particular, in practice an individual would be required to make an additional visit to the dental technician a couple of weeks ahead to get the cast made and making the cast is not a comfortable, nor patient-friendly process. Furthermore, the quality of geometry produced by one or more of the conventional techniques described in WO 02/08357 may be insufficient for some purposes but in some instances a more economical technique may be advantageous.

Thus there is a need for a method and apparatus which substantially ameliorates or overcomes the abovementioned disadvantages.

According to a first aspect there is provided a method of generating a model of a real object derived from a model of a second object, the model of the second object being defined by an array of data points, a number of identifiable components and a number of further components, the method comprising:
  measuring a number of parameters of a number of corresponding identifiable components of a real object corresponding to the number of identifiable components in the model of the second object;
  generating an array of data points defining a first model of the real object using a number of the measured parameters; and
  generating a further model of the real object, the step of generating the further model comprising the steps of:
  substantially aligning the model of the second object with the first model of the real object;
  placing a number of identifiable components represented in the model of the second object into positions corresponding to positions of equivalent components in the real object as defined by the measured parameters;
  placing a number of the further components represented in the model of the second object into positions on the first model of the real object to represent corresponding components in the real object; and
  adjusting the positions of one or more of the components placed on the first model of the real object to generate the further model of the real object.

Preferably, the step of adjusting comprises one or more of moving, scaling and/or rotating the components.

Preferably, the model of the second object is a model jaw, and the step of measuring a number of parameters of a number of corresponding identifiable components of a real object comprises measuring the parameters of a number of corresponding identifiable components of a real jaw.

In a preferred embodiment, the number of identifiable components comprise a number of teeth, and the further components comprise further teeth.

Preferably, the step of generating an array of data points defining a first model of the real object comprises creating an array of data points defining a first datum line curve corresponding to a curved shape of a jaw.

Preferably, the step of measuring a number of parameters of a number of corresponding identifiable components of a real object comprises measuring parameters of a number of teeth of a real jaw having a curved jawline. For example, the step of measuring the number of parameters may comprise measuring one or more of a centre of a furthest back remaining left tooth, a centre of a selected xth tooth, an apex point of the jawline curve, a centre of a selected yth tooth, and/or a centre of a furthest back remaining right tooth. Alternatively, the step of measuring a number of parameters of a number of corresponding identifiable components of a real object comprises stroking a sensor around a jaw line from a backmost existing tooth on one side to a backmost existing tooth on the other side. This step may be repeated a number of times to obtain many parameters describing the jaw line. The furthest back left data point may be considered to be indicative of the position of a back edge of a furthest back remaining left tooth and similarly for the right, and the apex point may be identified from the captured data.

Preferably, the step of placing a number of the further components comprises deleting one or more images of missing teeth.

In a preferred embodiment, the step of adjusting comprises scaling up to reduce one or more gaps between adjacent components except when said one or more gaps correspond to a missing tooth, and/or scaling down to reduce overlap between adjacent components, and/or rotating one or more components.

If a number of the placed further components overlap, the method may further comprise moving a number of the placed further components to reduce the sum of the distances overlapped by adjacent further components prior to the step of adjusting. Alternatively, the volume of overlap by adjacent further components may be reduced by moving a number of the placed further components prior to the step of adjusting. These processes may be repeated iteratively until a state of minimum overlap is achieved or the overlap falls below a predetermined threshold. The component(s) to be moved may be selected according to one or more criteria and may be selected using, for example, an algorithm.

Preferably, the step of moving comprises moving said number of further components dependent on the nature of said component or components, said moving being constrained by the nature of said component or components.

Preferably, the step of measuring comprises measuring the parameters using a sensor such as a six degrees of freedom probe.

In a preferred embodiment, the method further comprises storing one or more of the first model of the real object, the model of the second object, the measured parameters, the array of data points defining the first model of the real object, and the further model representing the real object.

Preferably, the step of storing comprises storing in a memory stage located in the processor in, for example, a memory stage located remote from the processor which may connect the memory stage to the processor through a communications network to transfer stored data, such as the Internet.

In a preferred embodiment, the storage stage comprises a database.

Preferably, the method further comprises generating a visual image of the real object from the further model of the real object.

According to a second aspect there is provided an apparatus for generating a model of a real object derived from a model of a second object, the model of the second object being defined by an array of data points, a number of identifiable components and a number of further components, the apparatus comprising:

a sensor to measure a number of parameters of a number of identifiable components of a real object corresponding to a number of the identifiable components in the model of the second object;

a generation stage to generate an array of data points defining a first model of the real object using a number of the measured parameters; and an operation stage to generate a further model of the real object, the operation stage being arranged to:

substantially align the model of the second object with the first model of the real object;

place a number of identifiable components represented in the model of the second object into positions corresponding to positions of equivalent components in the real object as defined by the measured parameters;

place a number of the further components represented in the model of the second object into positions on the first model of the real object to represent corresponding components in the real object; and adjust the positions of one or more of the components placed on the first model of the real object to generate the further model of the real object.

In a preferred embodiment, the second object comprises a jaw, and the number of identifiable components comprise a number of teeth, and the further components comprise further teeth. The parameters of a number of corresponding identifiable components of a real object may then comprise parameters of one or more teeth in a real jaw having a curved jawline.

The number of parameters may comprise one or more of a centre of a furthest back remaining left tooth, a centre of a selected xth tooth, an apex point of the curved jawline, a centre of a selected yth tooth, and a centre of a furthest back remaining right tooth. Alternatively, the number of parameters may comprise a back edge of a furthest back remaining left tooth indicated by the furthest back left data point and similarly for the right, and the apex point may be identified from captured data.

Preferably, the operation stage is arranged to move a number of the further components by deleting one or more images of missing teeth.

In a preferred embodiment, the operation stage is arranged to scale up to reduce one or more gaps between adjacent components except when said one or more gaps correspond to a missing tooth, and/or scale down to reduce any overlap between adjacent components and/or rotate one or more components.

Preferably, the sensor comprises a six degrees of freedom probe.

In a preferred embodiment, the apparatus further comprises a storage stage for storing one or more of the array of data points defining the model of the second object, the measured parameters, the array of data points defining the first model of the real object, and the further model representing the real object.

Preferably, the storage stage comprises a memory stage located in the processor, or alternatively a memory stage located remote from the processor. In the latter preferred embodiment, the storage stage may be connectable to the processor through a communications network such as the Internet.

Preferably, the storage stage comprises a database.

In a preferred embodiment, a number of the placed further components overlap, the operation stage being arranged to move a number of the placed further components to reduce the sum of distances overlapped by adjacent further components prior to adjusting. Alternatively, the operation stage is arranged to move a number of the placed further components to reduce the volume of overlap by adjacent further components by moving a number of the placed further components prior to the step of adjusting.

Thus, one or more preferred embodiments enable the generation of a customised/personalised representation of geometry and/or an object which is sufficiently realistic, from a standard model object, using only a minimal number of direct measurements of parameters of the real object. Furthermore, the generation of the representation may be in essentially real time, that is, it is accessible when needed in the application flow. In the context of this specification, the term "sufficiently realistic" may be considered to mean one or more of the following:

when displayed on a computer monitor and used within the computer application, the geometry is to be considered realistic enough from the perspective of the client whose teeth are being analysed; and/or the geometry is accurate enough for the scale of any comparison measurements being made with the system By comparison, conventional methods tend to be either unacceptably slow, expensive, manual, and/or inaccurate or a combination thereof. Typically, conventional methods may comprise:

manually making a physical cast of the client's teeth using plaster, manually scanning the teeth to create the geometry (or placing them in an automatic handling system)

safely storing & and ultimately safely disposing of these casts

The abovementioned conventional methods would also typically be carried out by a number of different skilled people, whereas by contrast, in the present invention, the process may be carried out by a single person, such as a dental hygienist.

One or more preferred embodiments of the present invention may be particularly advantageous when compared to conventional methods as, in conventional methods, creating and scanning teethcasts is not a robust, practical process given time and cost constraints. In practice, in the conventional methods, an additional visit by the patient would be required a couple of weeks prior to the date on which the scanning is performed, to enable the cast to be made. Furthermore, the making of the cast is not a comfortable patient friendly process. Whereas, in accordance with one or more preferred embodiments of the present invention, the process is quick and easy and comfortable for the client.

One or more embodiments of the methods and apparatus embodying the invention therefore provide a viable and practical capture technique and apparatus for use in various processes such as in clinical studies, dental care and training applications.

The present invention will now be described by way of example and with reference to the accompanying drawings in which.

Figure 4A:
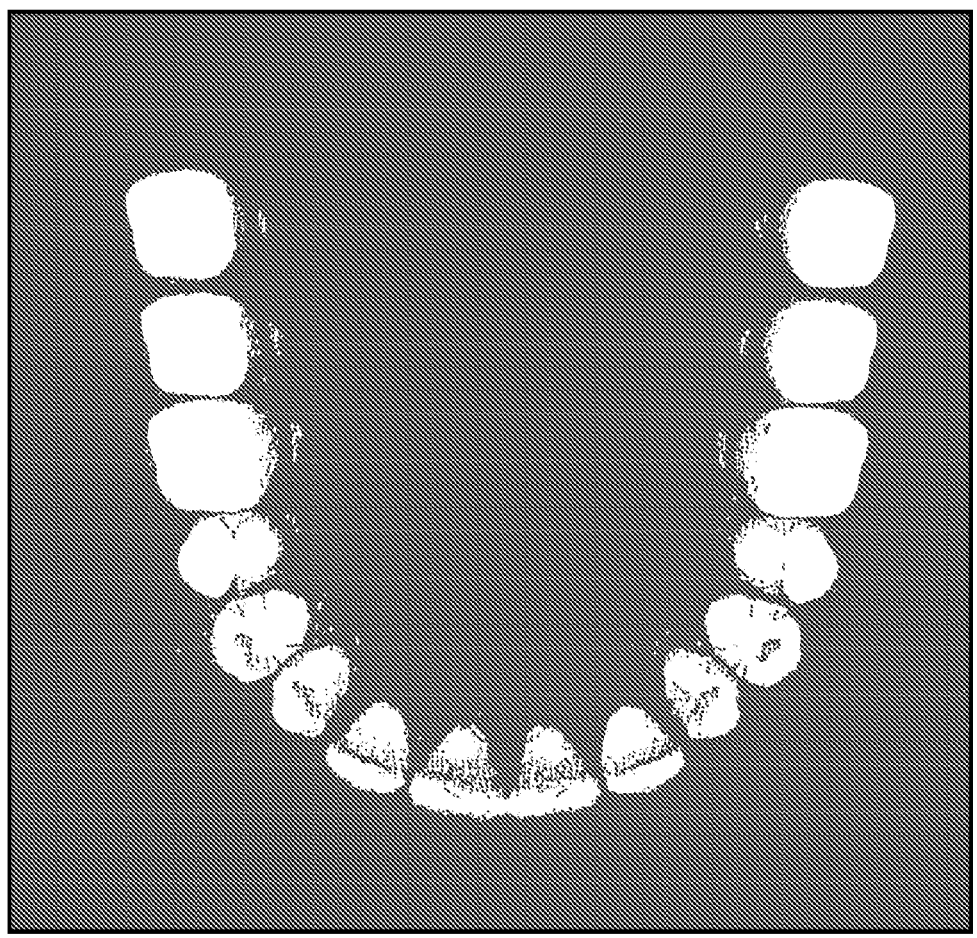
Figure 4B:
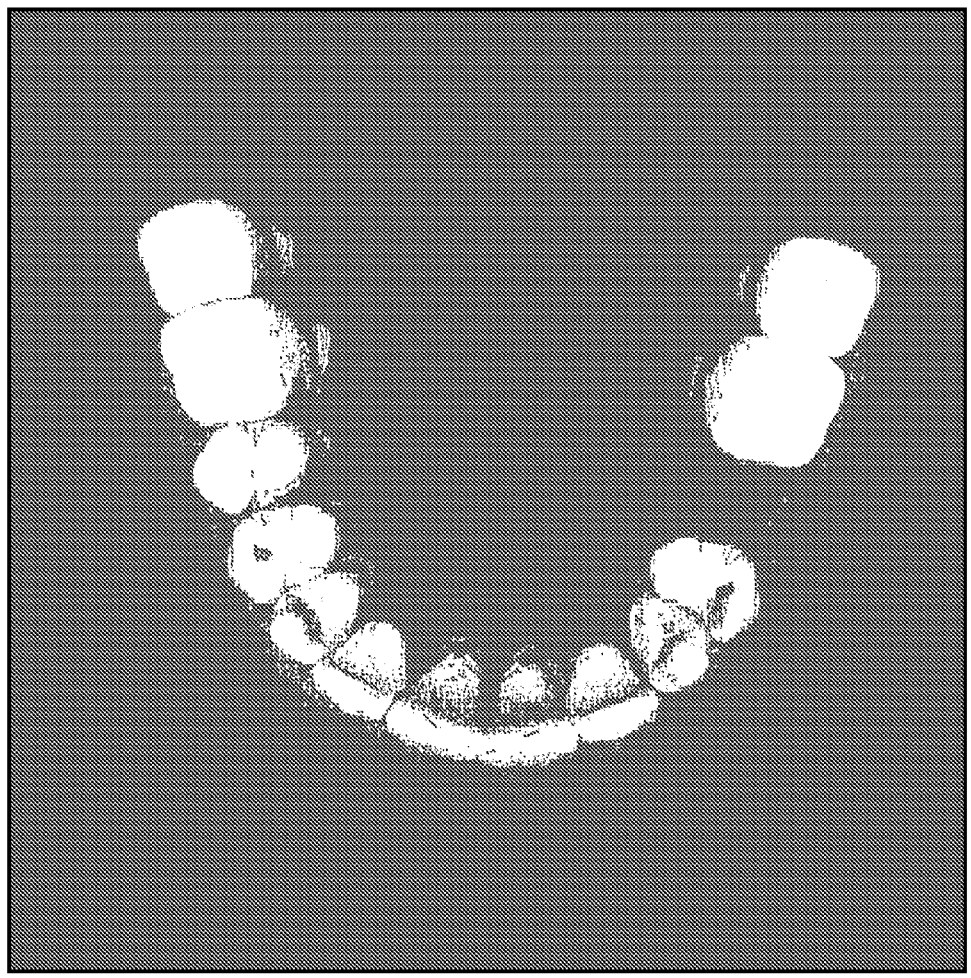
Figure 5:
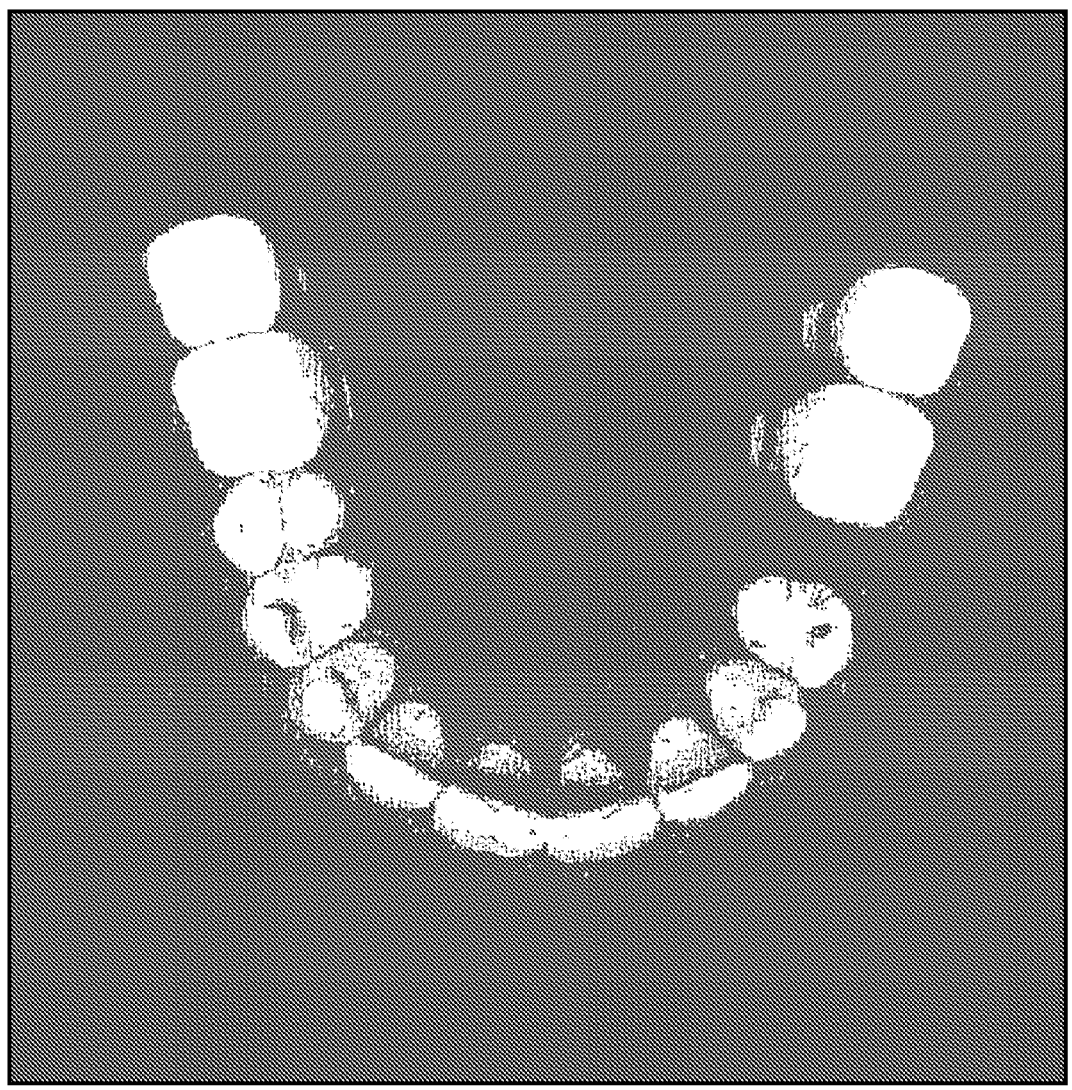
Figure 6:
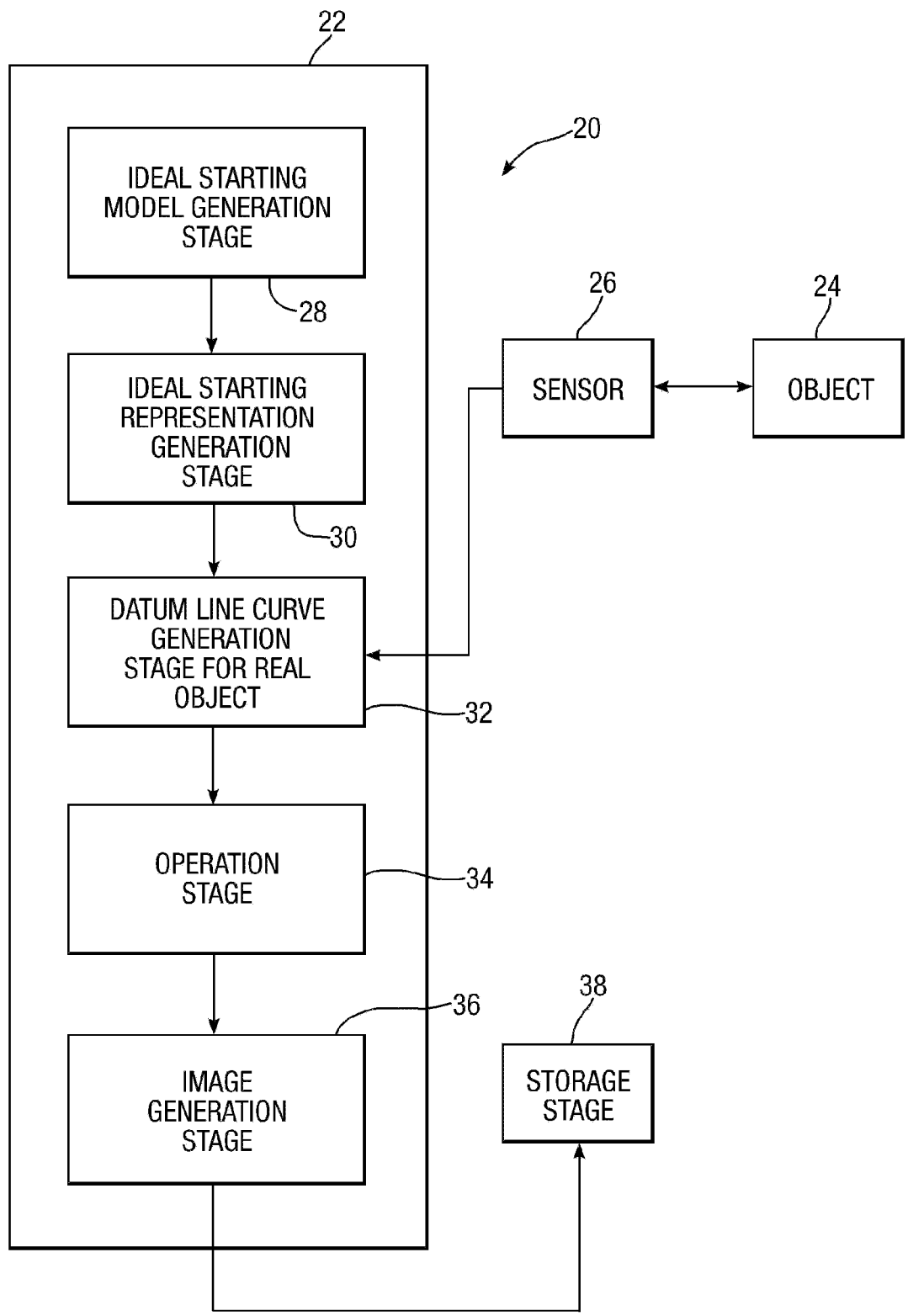

FIG. 4*a* is a perspective view from above of a representation of an ideal or standard model set of teeth in one jaw;

FIG. 4*b* is a perspective view from above of a representation of a stressed geometry, derived from the model teeth geometry of FIG. 4*a* and captured data;

FIG. 5 is a perspective view from above of a representation of a customised set of teeth in one jaw which is obtained from the representation in FIG. 4*b* using relaxation techniques; and FIG. 6 is a schematic block diagram showing the stages in apparatus according to a preferred embodiment of the present invention.

In a preferred embodiment of the present invention, information obtained from an individual client using a probe is used to generate a visual representation of a model jaw for that individual based on a stored model of a jaw and using the information obtained from the individual. The teeth depicted in the stored model may be represented as a "string of beads" on a one-dimensional datum line curve. Initially this is a perfect model "necklace". Several models may be stored in a database for adaptation according to the type of individual, for example, different models may be used for adults and children.

Figure 1:
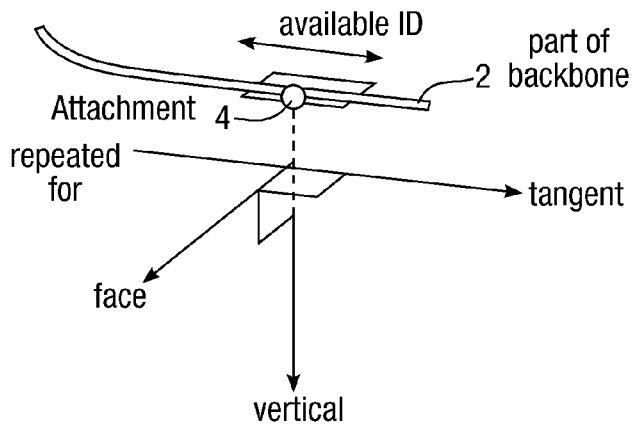
FIG. 1 is a two-dimensional graphical representation of part of a model for a teeth geometry set-up according to a preferred embodiment of the present invention.
Figure 2:
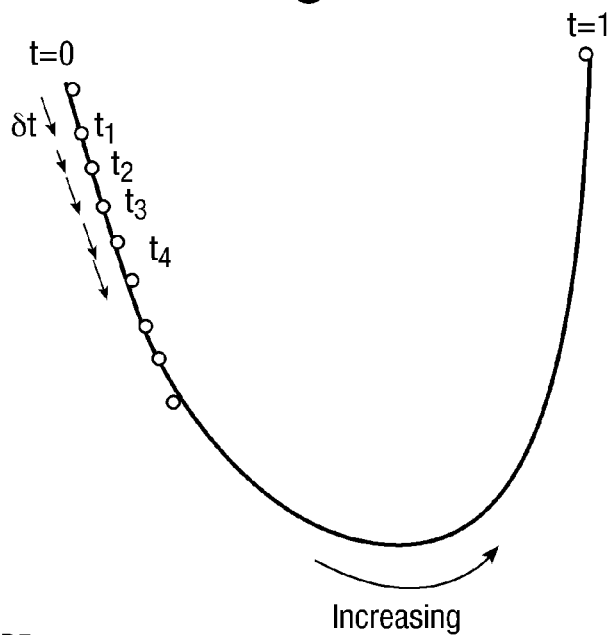
FIG. 2 is a schematic representation of the complete model of FIG. 1.

As shown in FIGS. 1 and 2, the datum line curve 2 is preferably U-shaped in two-dimensions and, in the model, the position 4 of each tooth is described by only one parameter (t) which represents the distance along the datum line curve 2 at which it is attached and, at this point, the tooth is imagined to hang vertically with the tooth face aligned with the appropriate tangent plane of the datum line curve 2 at that point. In this model, the teeth may only move (or jiggle) along the curve of the datum line 2, which is essentially a one-dimensional motion along a one-dimensional curve that is embedded in a three-dimensional space.

If the datum line curve 2 is described analytically, or in a numerically discrete way, as a function of the variable t [or, in the numerical case, in terms of small real steps δt], then the representation is said to be a parametric one. Given that representation, it is possible to obtain the tangent plane and face normal as a function of t, as will be described in more detail below.

As part of the initial set-up process and prior to first use on an individual, to obtain the initial model shown in FIG. 2 and part of which is shown in FIG. 1, a base parameterisation of the whole of each of the stored models is performed. This is not generally performed each time a new individual's model is to be generated, but is generally performed only once as part of the initial setting up of the system/device and prior to its first use on an individual.

The base parameterisation process is as follows.

Figure 3:
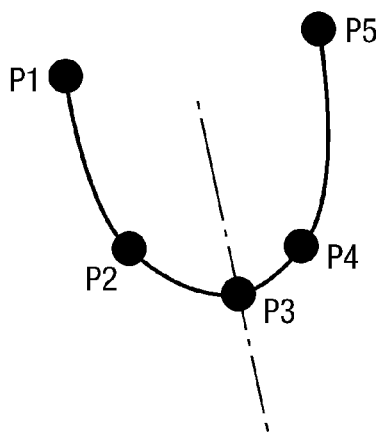
FIG. 3 is a parameterised numerical representation of ideal attachment points for teeth using a preferred embodiment of the present invention.

The datum line curve 2 is constructed by estimating the ideal attachment points 4 of the model teeth in the model teeth set, an example of which is given in FIG. 3, which is one of an upper or lower teeth set. The ideal attachment point 4 for each tooth may be obtained by projecting each tooth centroid up to the top of the teeth or down to the base of the tooth. The ideal datum line curve 2 may then be traced out through this set of points 4. An analytical curve may be fitted to this shape (because the shape is multi-valued it may be necessary to fit each half separately and merge), or alternatively and more usefully, a numerical contour may be made by calculating a number of equally spaced points t1, t2 . . . along the datum line curve 2, joining these points and interpolating to make an ordered set of line segments which represent the parameterised numerical representation of the model jaw. The numerical version of the tangent plane and normal may then be calculated from this contour using known mathematical procedures.

These segments are of equal length and should be a small fraction of the maximum distance by which it is chosen that an individual's tooth may be moved when generating the model of the individual's teeth.

The points t1, t2 . . . may be denoted by (X1, Y1, Z1), (X2, Y2, Z2) respectively where each of the X, Y, and Z co-ordinates are co-ordinates in the known model frame and are the same co-ordinates as those defining the polygon geometry used in generating a displayable image of the teeth.

The datum line curve 2 may be expressed as [X(t), Y(t), Z(t)]. The tangent plane to the curve at any given point (t) may be expressed using the gradient at [X(t), Y(t), Z(t)] and the normal to the curve 2 may be expressed using the vector product between the tangent plane and the unit vector in the vertical direction at the same point. It should be noted that this generalises straightforwardly when Z is non zero, that is, when the curve is not in a 2D plane. The unit normal at each point (t) may be pre-calculated and stored as a property of the curve, together with any specific rules associated with each point (t), for example, t>=0, t<=1 and, during the jiggle process no tooth may move to a value of t that takes it from one side of the jaw to the other.

t indexes each point along the curve in steps of t. Depending on situation, t may be considered to label explicit parameterised distances along the datum line curve 2 denoted by t=0, t, 2 t, 3 t . . . , . . . , N t, where N is number of segments. In a preferred embodiment, if N t=1, t may then be selected by selecting the value for N. Alternatively, t may be considered to index positions along the datum line curve 2, that is, t=0,1,2,3, . . . . N. It should be noted that t is defined on the ideal model geometry datum line curve 2, not on that derived from a real jaw so that if, for example, the back teeth are missing in the real jaw subsequently being studied, then empty segments at the back of the jaw will still have a t index.

For each individual tooth in the model jaw, it is advantageous to pre-calculate or pre-assign the following:

the model tooth geometry the model bounding box, that is the smallest cuboid that may be constructed which will exactly contain the model jaw the model tooth hanging point on the datum line curve expressed as an index into the t array.

how far each tooth is allowed to move or jiggle in either direction along the datum line curve expressed as number of "segments", not actual distance. This can be different for each type of tooth.

preferably how "sticky" the tooth is to its right and left neighbours, that is, whether or not there is a gap between the teeth.

The following tooth related properties are examples of properties which may also be set and used, however, other tooth related properties may also be set and used:

the overlap with the tooth on left
the overlap with the tooth on right
the free boundary on the left [True/False]
the free boundary on the right [True/False]

In this way, the datum line curve 2 and set of teeth may be created to represent a parameterised model jaw as shown in FIG. 4a.

The above-described process may then be repeated to generate the other model jaw (that is, either the lower or upper model jaw).

Various properties will be associated with the whole assembly comprising the parameterised upper and lower model jaws, such as the global (total) overlap for the jaw. The total overlap is the sum of individual overlaps.

The parameterised upper and lower model jaw representations may be created and stored, for example in a database, and then used subsequently as models for multiple individuals.

It may be advantageous to store separate adult and child versions of model jaws.

In the model jaw, as shown in FIG. 3, a predetermined number of points denoted, in this example, by P1, P2, P3, P4, and P5 on the model jaw datum line curve 2 are selected during the initial set-up process so that they are known a priori. FIG. 3 shows five capture points on the datum line curve having X, Y, Z co-ordinates, where P1 is the centre of the furthest back remaining left tooth (not the back of the gum), P2 is centre of a selected xth tooth, P3 is the apex point of the datum line curve, P4 is the centre of a selected yth tooth, and P5 is the centre of the furthest back remaining right tooth (not the back of the gum). A number of these points in the model geometry should preferably be pre-defined prior to obtaining any readings of an individual's teeth to be studied and this may therefore require an agreed definition of P2 and P4, that is, which teeth are to be considered as the xth and yth teeth respectively.

Whilst FIG. 3 shows five capture points, in a preferred embodiment only the points P1 and P5 may be selected, that is, the points denoting the furthest remaining back teeth on the left and right hand sides respectively.

The next stage in the process, according to a preferred embodiment of the present invention, is to generate a model jaw based for a particular individual based on the model jaw created in the above manner and measurements from a particular individual using very limited subject information. That information may include which teeth are missing in the individual, as evidenced by inspection or dental records, and collection of data for a predetermined number of points in the individual's dentition which may be captured by a probe. The collected points may include, the furthest remaining back teeth for each jaw, and may include other specific capture points, for example, the five capture points as shown in the standard model of FIG. 3, and may include a large number of non-specific points captured by the probe as it is moved around the jawline.

These points captured by the probe will provide the basic data describing the shape of the individual's jawline and define the real (as opposed to model) backbone datum line curve for the individual.

The probe which may be used to capture the information is preferably a six Degrees of Freedom (3 position+3 orientation) sensor which is preferably connectable to the processor being used via, for example, a PCI interface Card.

The process for generating a model of an individual's teeth according to a preferred embodiment is then as follows. A parameterised curve for an individual may be created in the same manner as described above for the model geometry, the only differences in creation being that only a pre-selected number of points (for example, the furthest remaining back teeth) on the datum line curve are used for the creation of the individual's model, whereas for the model geometry one point for each model tooth may be used. Furthermore, it is not necessary to access the real tooth centroid when creating the real model of the individual's teeth but it is necessary to define an equivalent point accessible by the probe.

In practice, during this process of capturing the data for the pre-selected number of points for an individual, many more than the pre-selected number of points will usually be captured, in fact a complete set of points may be captured by stroking the probe from the furthest remaining back tooth on one side of the jaw through to the furthest remaining back tooth on the other side of the jaw in the individual's mouth. However it is important that there is sufficient data captured. P1 and P5 should still be the end points of the data collection. This collection of points is then used to generate a U shaped datum line curve for the particular individual. In a preferred embodiment, it may be sufficient to identify the furthest back remaining teeth which define the end points of the data collection process and which teeth are missing, rather than explicitly identify points all points P1 to P5.

The captured data points for the individual will be in the frame of reference of the probe sensor, not the frame of reference of the model geometry. In order to bring the model datum line curve, with the model teeth set attached, into "rough" alignment with the individual's datum line curve prior to correlating P1 and P5, an iterative closest point algorithm such as that described in the applicant's European patent number EP 1 379149 B1 derived from International application published as WO02/083257 may be used. The use of such an algorithm permits the overlaying of the model datum line curve on the datum line curve for the individual by rotation and translation of the model datum line curve, without distortion of either datum line curve, until the two curves are in rough alignment with one another.

It is advantageous to define a predetermined number of segments on the individual's parameterised datum line curve and, if the backmost teeth on the left and right are present, this number is preferably exactly the same as the number of segments for the stored model datum line curve. However, if back teeth are missing in the individual under consideration, it is also true but it is necessary to work out how many of these segments are virtual gum segments extending beyond the back of actually existing teeth. The length of the segments and orientation thereof will be different from the model case. The number of segments may be controlled by interpolation.

The teeth required to be added to the datum line curve for the individual to form the model of the individual's jaw, may then be positioned onto the datum line curve generated for the individual, at the corresponding segment (defined by the value of t) in which those teeth are positioned in the model curve. The placement of the teeth may be achieved through copying representations of the teeth positioned on the model jaw onto the datum line curve for the individual. Missing teeth are not positioned on the individual's curve, the corresponding segment is thus left empty. The orientation of each tooth face may be given by the normal to the real curve, so an automatic rotation may be required. If the real segment length is less than the model segment length, this will produce an odd looking geometry with typically overlapping teeth, and if the real segment length is more than the model segment length, gaps between teeth will be shown at this point. A direct or approximate calculation of the overlap of each tooth and therefore the total overlap for each jaw may be calculated. To reduce complexity and simplify the calculation required, it is preferable to use the distance overlapped by the edges of adjacent teeth, not the volume overlapped, and this is considered to be sufficient for accuracy purposes. However, other methods of calculating the overlap may be used.

The geometry obtained by this process is shown in FIG. 4b and is termed the "stressed" or initial condition geometry. This geometry may then be refined into a final configuration by "relaxation" processes by which the teeth are moved or jiggled along the datum line curve for the individual and/or scaled to create a state of zero global overlap. When this state of zero global overlap is reached, within predetermined tolerance limits, the final geometry is considered to have been obtained. This step by step creation and customisation of the individual's model jaw may be displayed in substantially real time on a screen, as shown in FIG. 5. The customised jaw geometry for the particular individual may then be saved to a database and used subsequently. The process is repeated for the individual's other jaw. The jaw capture process is then complete.

A number of ways of implementing the relaxation process are possible and the above described process is merely one example.

An image such as that shown in FIG. 5 may then be created based on the output geometry within the user interface, as and when required, and the generated image gives the illusion of being a full 3D representation of the individual's teeth geometry, which can be interactively rotated and scaled as required, using, for example, a mouse.

Once a customised geometry has been created for an individual, it may be stored on a database and may be recalled from the database when desired, thereby eliminating the need to regenerate the image for that individual from scratch. Alternatively, if a new customised geometry is required for that individual, a new set of probe data may be collected and applied to the stored customised geometry for that individual rather than the standard model, to reduce processing complexity and increase the speed of the process.

FIG. 6 is a block diagram showing some of the stages in an apparatus 20 or system embodying a preferred embodiment of the present invention. The processor 22 comprises a plurality of stages which process data received from the measurements made on the object 24 which are captured via the sensor 26 which is preferably a six degrees of freedom probe. The processor 22 comprises a first array generation stage 28 in which the ideal starting model geometry is loaded from a storage device. In the next stage 30, the representation of the ideal model datum line curve is generated from the ideal model geometry and parameters associated therewith. Then, the datum line curve of the real object 24 is generated in a further stage 32 based on data captured by the sensor. An operation stage 34 carries out the various operations of roughly aligning the model datum line curve with the datum line curve of the real object 24, and then copying a number of representations of teeth on the model into various positions on the datum line curve of the individual and scaling as desired and as described above in connection with FIGS. 1 to 5. A model, which may be in the form of a visual image, of the real object may then be generated in a further stage 36 based on the output from the operation stage 34. This may then be stored in a storage stage 38 in a storage space which could be within the processor 22 or remote therefrom.

The storage stage 38 could be a memory including a database and, if remote from the processor 22, could be connectable thereto via a communications network such as the Internet to transfer data concerning the generated image between the processor 22 and the storage stage 38.

In a preferred embodiment, the model may be generated in stages 28 and 30 which are located in a processor remote from the processor which is arranged to generate the model of the real object 24 based on measurements obtained using the sensor 26 and the data may be stored and transferred to that processor for subsequent image generation Preferably, there are some rules that may constrain the process embodying the present invention, including, for example:

(a) No tooth may move or 'jiggle' further (in terms of segments) than that prescribed for its tooth type.
(b) No tooth may move from right round to left and vice versa.
(c) No additional segments may be created for teeth to move onto.
(d) For aesthetic reasons particular care may need to be taken with front teeth.
(e) At any point in the relaxation process
  No move can happen that increases the total overlap
  Only teeth with free edges may move and only in the direction of the free edge
  Every possible move must be exhausted and there still be global overlap before a scale may be attempted.
(f) For gaps between teeth, it may be desired to drive these teeth back together by enforcing a rule that teeth that are there and adjacent must have no gap between them (that is, they are termed "sticky"). This is a complication, but a surmountable one which may be addressed by scaling the initial stressed configuration, prior to moving the teeth; and
(g) The tooth with most overlap (and can be moved) is moved first.

There are also a number of parameters that may be fixed to obtain a "smooth" move, for example, the size of permissible movement step. Other parameters which may be set control the speed and required accuracy of the process. These parameters may be changed via, for example, a user interface, particularly if optimisation is required and they may be input each time the algorithm is used, via the intuitive user interface.

Data indicating which teeth are missing in the (real) individual's dentition may be input each time the algorithm is used, either manually following a visual inspection by the clinician or reference to the individual's data records, or from the probe data describing the jaw/teeth arrangements of that individual. This input of data may be made by a user using the probe system but may preferably be preloaded onto the system before a particular study. This information may be input into a processor through a user interface using, for example, a mouse to click on pictures of the missing teeth.

In practice, motion sensors may be attached to the client and to the probe used to determine the pre-selected points in the client's jaws. The stored version of the model jaw may be displayed on a display device such as a computer screen and data provided by the clinician may be used to denote missing teeth corresponding to those missing in the individual under consideration. The stored model jaw and the individual's model jaw may be rotated, and/or scaled and/or translated in real time using the mouse, in order to get the most useful view. The clinician places the end of the probe in the individual's mouth, such that it is in contact with the corresponding set of the individual's teeth, then clicks a button on the probe which turns on the data capture process. The probe may then be stroked around the individual's set of teeth to capture the shape of the individual's jaw. Should the clinician wish, the probe button may be clicked to stop capture and then re-clicked to start capture again, the data streams being added together.

In practice, the process may be controlled through a customised user interface coupled with a control button on the probe used for obtaining measurements from an individual. These are used together to take the clinician through the process of creating the customised jaw geometries for the individual. The user interface may comprise a series of panels displayed on a display device connected to the processor which guide the clinician through the process, step-by-step.

Once the capture process is complete, the data identifying the captured points may be input into the processor and these points may be displayed visually, for example as a set of red markers. Prior to display, an initial calculation may be performed using the iterative closest point algorithm to align approximately the model jaw and the captured data for the individual. Again this complete visualisation may be rotated and/or scaled and/or translated, and may be seen by the individual, if desired.

An example of a method of implementing the above described process of adapting the model jaw for an individual may be as follows:

Firstly, the parameterised model may be loaded into the user's processor, then the parameters defining the movement process are initialised. The data obtained from an individual's jaw using a sensor such as a probe is collected and/or accessed, if pre-stored, together with missing teeth information for the particular individual under consideration. From this, the initial "stressed" geometry is computed. If the model geometry is smaller than the real geometry which creates a number of 'gaps' between adjacent teeth, then the teeth geometries are scaled upwards until the gaps disappear, even if this then creates some overlaps between adjacent teeth. This gives a new 'stressed' geometry. From this new stressed geometry, it is possible to compute the total amount of overlap in the model for the individual together with the overlap for each tooth and the proportion of the overlap to the left and right of each tooth. When the overlap determined is greater than the permitted tolerance, the teeth which may be moved are determined together with the teeth which are most overlapped, the overlap being based, at least initially on the bounding box geometries. If there are no movable teeth determined but the overlap is still greater than the permitted tolerance, the teeth may be rescaled to a smaller size. The rescaling may only affect the real X,Y,Z coordinates of the teeth rather than affect the position of the teeth along the datum line curve 2. The teeth may then be moved individually to reduce the overlap to within the tolerance level.

After processing, the individual's model comprises a new data object containing the customised teeth geometry and this may be stored as a separate data file from the original model so that all the original model data remains in the database, without corruption and may be used for other individuals. The new data object for a particular individual may be stored in the data base and may be recalled as required for other applications. Alternatively, the probe data and settings for an individual may be saved, and the individual's model jaw may be regenerated from this data at a later stage, as this would be sufficient to regenerate the customised geometry and would not require as much storage space as saving the individual's entire teeth geometry.

The database may be in a storage medium in the processor being used by the clinician or may be remote therefrom and linked to the processor by a network, for example, a LAN or the Internet. The data may be transferred to a central storage facility which may be accessible worldwide for reference purposes and data from other sources may be added to it to establish a large database of teeth models. This would have particular advantages in industry, as it may enable, for example, large trials of new tooth brushing designs to be conducted. Dentists may be supplied with the toothbrush/toothpaste combination to be tested and the data collected via the network connection for secure analysis. Also, the data and insights could be exchanged.

Thus, one or more embodiments of the present invention are particularly advantageous as they enable the generation of a set of realistic teeth geometries for an individual, in essentially real time, using the bare minimum of additional data.

As mentioned above, more than one set of standard geometry may be pre-loaded, for example, a model set of adult teeth and a model set of child teeth may be included. These models are preferably not hard coded, and a mechanism may be provided within the user interface for enabling the user to select which model is to be used if more than one potential model is available.

Various modifications to the embodiments of the present invention described above may be made. For example, other components and method steps can be added or substituted for those above and the order in which the steps are performed may be altered. Thus, although the invention has been described above using particular embodiments, many variations are possible within the scope of the claims, as will be clear to the skilled reader, without departing from the scope of the invention. In particular, whilst the above preferred embodiments have been described in the context of generating model jaws for an individual, the process is note to be considered as being restricted to teeth, but could be used in any situations where it is desired to rapidly create reasonably good 3D computer representations of real objects using only limited captured probe data about those real objects. A good "standard" model of an object which can be used as the starting point for the creation of the representation of the real object through a process of controlled customisation is necessary and, in deforming the standard model with the algorithm using the probe data, the result is likely to be good if the instances of the real object naturally scale. In the context of teeth, this enables the height of the teeth to appear realistic in the final result even though the height of the teeth is not measured in the process. Such situations are, in general, more often to be found with naturally formed objects. However, the process embodying the present invention may be applied to other applications including the use of customisations of standard geometries, to personalise computer games. Furthermore, the process embodying the present invention may be used to create realistic teeth geometries which may be used together with motion tracking data from a brush and jaws, to make sufficiently accurate measurements of toothbrush position/orientation relative to teeth and create sufficiently believable on-screen representatives of all the motions.

The invention claimed is:

1. A method of generating a model of a real jaw derived from a model jaw, the model jaw being defined by an array of data points, a number of teeth and a number of further teeth, the method comprising:

measuring a number of parameters of a number of teeth of the real jaw, the real jaw having a curved jaw line, the number of parameters corresponding to a number of teeth in the model jaw;

generating an array of data points defining a first model of the real jaw using a number of the measured parameters; and generating a further model of the real jaw, the step of generating the further model comprising the steps of:

aligning the model jaw with the first model of the real jaw;

placing a number of teeth represented in the model jaw into positions corresponding to positions of equivalent teeth in the real jaw as defined by the measured parameters;

placing a number of the further teeth represented in the model jaw into positions on the first model of the real jaw to represent corresponding teeth in the real object; and adjusting the positions of one or more of the teeth placed on the first model of the real jaw to generate the further model of the real jaw; wherein the step of measuring comprises measuring the parameters using a sensor comprising a six degrees of freedom probe connected to a processor configured to process data received from the sensor.

2. A method according to claim 1, wherein the step of generating an array of data points defining a first model of the real jaw comprises creating an array of data points defining a first datum line curve corresponding to a curved shape of the real jaw.

3. A method according to claim 1, wherein the step of measuring the number of parameters comprises measuring one or more of a centre of a furthest back remaining left tooth, a centre of a selected xth tooth, an apex point of the curved jaw line, a centre of a selected yth tooth, and/or a centre of a furthest back remaining right tooth.

4. A method according to claim 1, wherein the step of measuring the number of parameters comprises stroking the sensor around the curved jaw line from a backmost existing tooth on one side of the jaw line to a backmost existing tooth on an opposing side of the jaw line.

5. A method according to claim 1, wherein the step of placing a number of the further teeth comprises deleting one or more images of missing teeth.

6. A method according to claim 1, wherein the step of adjusting comprises scaling up to reduce one or more gaps between adjacent teeth except when said one or more gaps correspond to a missing tooth, and/or scaling down to reduce any overlap between adjacent teeth, and/or rotating one or more teeth.

7. A method according to claim 1, wherein a number of the placed further teeth overlap, the method further comprising moving a number of the placed further teeth to reduce the sum of the distances and/or volumes overlapped by adjacent further teeth prior to the step of adjusting.

8. A method according to claim 1, wherein the step of adjusting comprises one or more of moving, scaling and/or rotating the teeth.

9. A method according to claim 1, wherein the step of moving comprises moving said number of further teeth dependent on the nature of said tooth or teeth, said moving being constrained by the nature of said tooth or teeth.

10. A method according to claim 1, further comprising storing one or more of the first model of the real jaw, the model jaw, the measured parameters, the array of data points defining the first model of the real jaw and the further model representing the real jaw.

11. A method according to claim 1, wherein the step of storing comprises storing in a memory located in the processor.

12. A method according to claim 1, wherein the step of storing comprises storing in a memory located remote from the processor.

13. A method according to claim 1, further comprising connecting the memory to the processor through a communications network to transfer stored data.

14. A method according to claim 1, wherein the communications network comprises the Internet.

15. A method according to claim 1, wherein the storage stage comprises a database.

16. A method according to claim 1, further comprising generating a visual image of the real jaw from the further model of the real jaw.

17. An apparatus for generating a model of a real jaw derived from a model jaw, the model jaw being defined by an array of data points, a number of teeth and a number of further teeth, the apparatus comprising:

a sensor comprising a six degrees of freedom probe configured to measure a number of parameters of a number of teeth of a real jaw real jaw having a curved jaw line, number of parameters corresponding to a number of the teeth in the model jaw;

a processor connected to the sensor and configured to receive data from the sensor, the processor comprising:

a generation stage to generate an array of data points defining a first model of the real jaw using a number of the measured parameters; and an operation stage to generate a further model of the real jaw, the operation stage being arranged to:

substantially align the model jaw with the first model of the real jaw;

place a number of identifiable components represented in the model jaw into positions corresponding to positions of equivalent components in the real jaw as defined by the measured parameters;

place a number of the further teeth represented in the model jaw into positions on the first model of the real jaw to represent corresponding teeth in the real jaw; and adjust the positions of one or more of the teeth placed on the first model of the real jaw to generate the further model of the real jaw.

18. Apparatus according to claim 17, wherein the first model of the real jaw comprises a datum line curve corresponding to the shape of the curved jawline.

19. Apparatus according to claim 17, wherein the number of parameters comprises one or more of a centre of a furthest back remaining left tooth, a centre of a selected left tooth (xth tooth), an apex point of the curved jaw line, a centre of a selected right tooth (yth tooth), and/or a centre of a furthest back remaining right tooth.

20. Apparatus according to claim 17, wherein the number of parameters comprises an edge of a backmost existing tooth on one side of the jaw line and a backmost existing tooth on an opposing side of the jaw line.

21. Apparatus according to claim 17, wherein the operation stage is arranged to move a number of the further components by deleting one or more images of missing teeth.

22. Apparatus according to claim 17, wherein the operation stage is arranged to scale up to reduce one or more gaps between adjacent teeth except when said one or more gaps correspond to a missing tooth, and/or scale down to reduce any overlap between adjacent teeth, and/or rotate one or more teeth.

23. Apparatus according to claim 17, further comprising a storage stage for storing one or more of the array of data points defining the model jaw, the measured parameters, the array of data points defining the first model of the real jaw, and the further model representing the real jaw.

* * * * *